United States Patent [19]
Francis, Jr.

[11] Patent Number: 4,756,311
[45] Date of Patent: Jul. 12, 1988

[54] MICROWAVABLE THERMAL COMPRESS AND METHOD OF USE THEREOF

[75] Inventor: Sam E. Francis, Jr., Ft. Pierce, Fla.

[73] Assignee: Jack Frost Laboratories, Inc., Sarasota, Fla.

[21] Appl. No.: 734,588

[22] Filed: May 15, 1985

[51] Int. Cl.⁴ ............................................. A61F 7/08
[52] U.S. Cl. .................................. 128/403; 126/204; 156/DIG. 108; 165/46
[58] Field of Search .................. 128/402, 403; 62/530; 126/204; 156/DIG. 108; 165/46

[56] References Cited

U.S. PATENT DOCUMENTS

| | | | |
|---|---|---|---|
| 3,804,077 | 4/1974 | Williams | 128/403 X |
| 3,874,504 | 4/1975 | Verakas | 128/403 X |
| 4,462,224 | 7/1984 | Dunshee et al. | 128/403 X |
| 4,488,552 | 12/1984 | McCann et al. | 128/403 X |
| 4,596,250 | 6/1986 | Beisang et al. | 128/402 |

Primary Examiner—Anton O. Oechsle
Attorney, Agent, or Firm—Mason, Fenwick & Lawrence

[57] ABSTRACT

Microwavable instant and/or cold pack gel package including an envelope fabricated from a laminate, for example, of films of synthetic resins and an aqueous gel in said envelope.

13 Claims, 1 Drawing Sheet

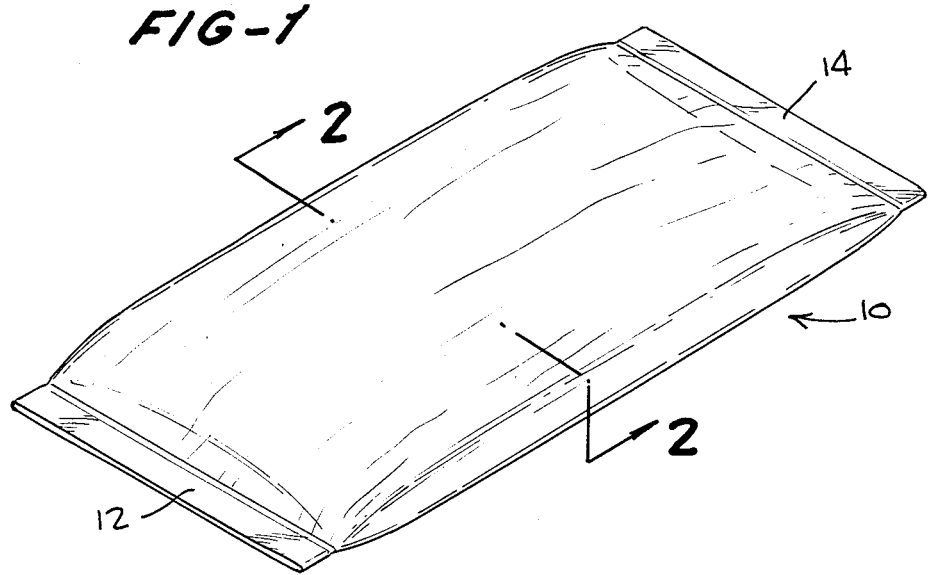
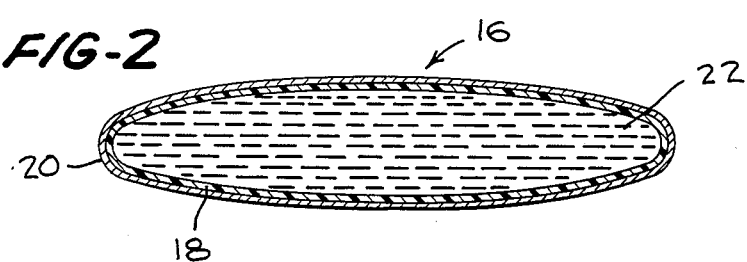

MICROWAVABLE THERMAL COMPRESS AND METHOD OF USE THEREOF

FIELD OF INVENTION

This invention relates to a thermal compress capable of being heated quickly by microwave energy without adversely affecting the components of the compress.

DESCRIPTION OF THE PRIOR ART

Thermal compresses including a plastic envelope containing a gel capable of maintaining its gel-like consistency over a wide temperature range are known as evidenced by U.S. Pat. No. 3,885,403 granted May 27, 1975.

Hot and cold packs including a rupturable container constructed of a laminated plastic sheet material including an outer layer of polyethylene terephthalate (Mylar) and an inner layer of low density polyethylene is disclosed in U.S. Pat. No. 3,763,622 granted Oct. 9, 1973. Hot and cold packs including containers or envelopes formed from laminates are also disclosed in U.S. Pat. No. 3,893,834.

BACKGROUND OF THE INVENTION

The thermal gel pack as disclosed herein is capable of various uses, such as to warm the hands or to warm or cool an injured or painful part of the body.

In use the pack or envelope to be utilized as a hot compress has been placed in hot water, however this procedure of heating the gel pack has not been entirely satisfactory from a stand point of thermal efficiency and convenience of use. As the pack attains the temperature of 212° F. thereby requiring tongs or the like for removal from the boiling water and the pack, being wet, is undesirable for its intended purpose, and requires drying thereof prior to use.

In addition heating of the water to the boiling point requires a fairly long period of time as distinguished from the significantly shorter time of heating of the pack by microwave energy as the pot or container for the pack must be fairly large for acomodating the pack without the pack touching the usual metal sides of the pot which would melt and damage the plastic envelope of the pack. This size pot would necessitate utilizing a large quantity of water thereby requiring a longer period of time for heating the water to its boiling point. Furthermore, when heating a gel package in boiling water in a pan or pot on a heater unit, the pan would be at the highest temperature which would damage, as by melting the plastic, present packages as the operator has no control over the pan temperature. Additionally when utilizing a large pan containing a large volume of water, the gel pack contacted the sides and bottom of the pan which were at a higher temperature than the water thereby resulting in damage to the envelope of the gel pack.

To overcome these deficiencies, applicant heats the pack by microwave energy in a microwave oven, however, the prior art gel envelopes were found to be entirely unsatisfactory since the thin plastic material utilized in the fabrication of the envelope developed pin holes in the plastic thereby resulting in discharge of the gel therefrom. Other deficiencies of the prior art envelopes are set forth below. To overcome the inadequacy of the compositions of the envelopes of the prior art applicant has invented a novel gel pack.

SUMMARY OF THE INVENTION

The primary object of the invention is a novel process for heating a gel pack by microwave energy.

One object of the invention of heating a gel pack by microwave energy is avoiding immersion of a gel pack in a material such as boiling water, with resultant adherence of the material to the envelope containing the gel which requires removal thereof with resultant loss of time or necessitating drying for removal of water which sequential operations, are, in a sense messy, and, should be avoided.

A further object of the invention resides in an envelope fabricated of materials capable of maintaining its integrity when heated by microwave energy over a relatively short period of about one (1.0) minute thereby permitting utilization of polyethylene envelopes without consequential tackiness or stickiness thereof and thus being capable of selecting a heating period with a safety factor of about two (2) minutes.

Another object of the invention is in a plastic envelope containing a gel composition including water wherein the material forming the envelope is a laminate including thin resinous film capable of not being adversely affected as by puffiness by resultant steam produced by microwave energy.

Yet another object of the invention is in the discovery that where foam insulation is employed in the gel envelope the insulation does not melt by applying microwave energy thereto as there is a reduction of heat loss at the side including the foam insulation. This foam insulation thereby permits a person to hold in comfort the gel pack at the area of insulation which otherwise may burn or be uncomfortable.

Still another object of the invention achieved by heating th gel by microwave energy is in enabling testing of the gel pack for heat and in easily returning the gel pack to the source of microwave energy thus being able to continue treatment over a longer period of time.

Still another object of the invention is a thermal pack having cosmetic use for opening the pores of the skin as in beauty treatments and dermatological uses.

Still a further object of the invention is a thermal pack which will not burn the human skin when removed from the microwave oven.

Still further objects of the invention will be readily apparent to those skilled in the art in light of the following description of the invention.

BRIEF DESCRIPTION OF THE DRAWING

FIG. 1 illustrates a schematic perspective view of a gel pack embodying the teachings of the subject invention.

FIG. 2 is a view taken along lines 2—2 of FIG. 1.

DETAILED DESCRIPTION OF THE INVENTION

Referring to the Figures, numeral 10 refers generally to a sealed plastic envelop sealed, for example, at both ends 12,14 or down the back by conventional procedures, e.g. heat sealing, dielectric treating, etc. The envelope 10 is fabricated from a stretchable laminate 16 of a pair of co-extensive films 18, 20 contacting each other throughout their surface areas and obtained from DuPont of Canada. One embodiment of the laminate 16 includes an inner film 18 of polyethylene having a thickness of two (2) mils and an outer layer or film 20 either of nylon or nylon sclair of about the same thickness as the polyethylene film.

In another embodiment of the invention, the inner film 18 is nylon sclair which seals good and the outer film 20 is of nylon.

In a still further embodiment the inner film 18 may be an individual resinous film or coating of polyethylene or polyurethane and the outer layer 20 is of paper or a fabric, for example, of nylon fabric.

The envelope 10 contains a liquid or paste or gel which has a low freezing point and a high boiling point and is preferably a gel having the following formulation.

| | | |
|---|---|---|
| 1350 gms. Carbopol TM | .7 o/o | |
| 13.5 gal. propyleneglycol | 27 o/o | |
| 180 gms. color dye | 0.09 o/o | |
| 1400 gms. formaldehyde | 0.2 o/o | |
| 2000 gms. sodium hydroxide | 1.0 o/o | |
| 37.5 gal. water | 71.7 o/o | |

This gel is formed as follows:

Initially, a dye mix is formed including 22 grams of a food coloring dye added to two (2) quarts (4.17 lbs.) of water and the sodium hydroxide mix is formed including 400 grams of flake sodium hydroxide added to one gallon (8.337 lb.) of water.

The dye mix and sodium hydroxide mix are added to an aqueous solution of Carbopol including the quantities as above stated and thereafter propyleneglycol and formaldehyde are added. The solution is agitated to achieve a uniform admixture.

The propylene glycol is a freezing point depressant and sodium hydroxide functions as a neutralizing agent.

Gel compositions other than the above, such as the gel compositions disclosed in U.S. Pat. No. 4,462,224 in col. 1, lines 45–55, may be utilized in the microwavable pack, which disclosure is herein incorporated by reference.

The envelope is sealed at one end 12 or in the middle (back seam) and the gel placed in the envelope at the opposite end which after the filling the envelope with an adequate quantity thereof is sealed at 14.

The laminate selected in the fabrication is critical as it must not be deleteriously affected by the microwaves during heating of the envelope.

EXAMPLES OF UNEXPECTED RESULTS

The following tests were made in the following microwave ovens operating at full power of about 750 watts employing the gel formulation on page 3 above. Amana #RRLSD, 120 v, 60 hz, frequency of 2450 mhz and a current power of 1500 watts, Tappan Model 56-4887 and Toshiba, Model No. ER-875BT.

TEST 1

A=laminated envelope of outer film of one mil Nylon and inner film of two mil polyethylene made by DuPont of Canada.

B=single prior art film envelope of polyethylene having a thickness of about 4 mils.

C=laminated envelope of outer film of 1 mil Nylon and inner film of 2 mil Nylon-Sclair.

D=high density modified rubber

E=outer nylon fabric layer laminated to inner layer of polyurethane.

F=outer paper fabric layer laminated to an inner layer of polyethylene.

| Material | Time In Microwave Oven in One Minute Intervals (Oven initially at ambient) | Temperature °F. | Results |
|---|---|---|---|
| A | 1 | 106 | Comfortable and soothing |
| | 2 | 140 | Comfortable and soothing |
| | 3 | | Comfortable and soothing |
| | 4 | 172 | Puffed up about 50 1/1. Seals and bag still intact - retained memory; no pin holes formed. |
| B | 1 | | Comfortable |
| | 1.5 | | Polyethyelene started puffing was tacky. |
| | 2.0 (took out) | | |
| | 2.5 (stopped) | | Soft and tacky, pin holes developed and envelope leaked did not retain memory. |
| C | 1 | | Warm. |
| | 2 | | Slight puff and hot |
| | 2 min. 52 sec. | 170° F. | Fully blown up. There was no leak and it retained memory. |
| D | | | Test similar to C but retained shape 40 sec. longer. |
| E | 1 | 110° | Started to slightly puff |
| | 2 | 156° | Two third's puffy |
| | 2.5 | 160° | About to explode |
| F | 1 | 106° | Slight puff |
| | 2 | 144° | Medium puff |
| | 2.56 | 185° | Tendency to blow up |

Where material A remained in the microwave oven continuously for two (2) minutes the material puffed up like a balloon at 198° F.

Where material E remained in the microwave continuously for two minutes and fourteen seconds, the material puffed up so much, it was ready to explode, as it reached a temperature of 177° F.

The tests with material A established:

1. One could heat the plastic laminated envelope in one minute increments and safely attain the desired temperature;

2. Although the bag puffed up at the end of four minutes, the seals and bag reamined intact; and a maximum temperature of 172° F. was attained;

3. The plastic retained its elastic memory at each incremental time period;

4. No pin holes resulted; and

5. When rupturing occurred in excess of four minutes, rupturing only occurred at the seam or seal with resultant oozing out of the gel.

The tests with material B established:

1. Polyethylene plastic exhibits a slight puff after one (1) minute and when replaced for 0.5 minute was hot and was tacky after two minutes (after 1st one minute and 2nd one minute);

2. That the opposed films of polyethylene stretched and thereby preventing reuse of the envelope bag;

3. Pinholes developed at 2.5 minutes (after 1st one minute and after 2nd one minute) thereby resulting in discharge of the gel from the plastic envelope;

4. The polyethylene had a loss of elastic memory; and

5. Melting of the polyethylene occurred at the temperature normally used to heat the package.

One test of a gel package formed of a laminate including Mylar established the unsuitability thereas as pinholes formed therein in less than one minute when subjected to microwave energy causing discharge of the gel from the package although additional 3–4 tests did not duplicate the same.

The tests established that the laminated plastic bags of materials A, C, D, E and F above could be heated by microwave energy in a microwave oven at a wattage output of about 750 and still retain their integrity without rupture or formation of pin holes at a period of time in excess of about 2.0 minutes whereas other laminates are incapable of use in a microwave oven.

TEST 2

In this example the envelope fabricated of the materials A utilized in Test 1 included therein "White Florida Sand" previously dried to remove moisture and ethylene glycol. The temperatures were measured after each one minute interval with the following results.

| Time Interval in Minute Increments | Temperature °F. | Observation |
| --- | --- | --- |
| 1 | 136 | No puffing |
| 2 | 182 | No puffing |
| 3 | 224 | No puffing |
| 4 | 252 | No puffing |
| 5 | 260 | Slight puffing |

Where the envelope was continuously heated for 3 minutes and 15 seconds at 250° F. only slight puffing occured which established the utility of this pack.

Use of propylene glycol by itself without white sand was impractical as it causes running and is undesirable.

TEST 3

Heat transfer material is an admixture of 5 percent hydroxyethyl cellulose and 95 percent propylene glycol in an envelope formed of the materials A in Test 1.

| Time Interval in Minutes Increments | Temperature °F. | Observation |
| --- | --- | --- |
| 1 | 153 | No puff |
| 2 | 226 | No puff |
| 3 | boiled | burst envelope |

It should be noted that microwave ovens include timers which function as a safety factor for controlling the degree of heat resulting from the application of microwave energy to the gel pack including the plastic envelope.

The practicality of the invention is readily evident as a user of the invention can readily apply cold and hot compresses to the body in time intervals shorter than that of the prior art which teaches heating the bag only in hot water as compared to quick heating in a microwave oven at one minute and two minute intervals to the compress and the resultant temperature is less than 212° F. on the external surface of the envelope and thus can be removed and manually handled.

Although the disclosure above relates solely to a gel pack thermal pack, the invention herein is applicable to a chemical thermal pack as disclosed in U.S. Pat. No. 3,874,504 to Verakas, wherein the intermediate envelope 11 can be made identical in composition to envelope 10 of the invention in this application. After the chemical thermal pack of Verakas has been utilized, it is no longer capable of functioning as an instant chemical thermal pack, however, by use of the laminated envelopes of the invention, the pack can be subsequently heated by microwave energy in the manner above and still achieve the unusual results attending the invention.

It is evident from the above disclosures that other modifications are within the scope thereof without departing from the spirit of the invention or sacrificing the principle advantages as set forth herein.

What I claim is:

1. A process of microwave heating a gel pack comprising the steps of:
    providing a gel pack comprising a completely sealed envelope constructed from opposed laminate layers portions of which are joined by sealed seams, said layers defining an inner chamber within which is disposed a gel that includes water, said chamber being sealed from the exterior of said gel pack, each of said laminate layers including a pair of co-extensive inner and outer films contacting each other throughout their surface areas, said films being of dissimilar materials;
    applying microwave energy of approximately full power of a microwave heating device to said gel pack for heating said gel to a desired temperature; and
    selecting the dissimilar materials so that the laminate layers of said gel pack do not pass steam produced during heating of said gel pack and do not rupture or separate at the seams thereof when subjected to said microwave energy for a period of time exceeding about two minutes but not exceeding about four minutes.

2. A process as set forth in claim 1, wherein said dissimilar materials are synthetic resins.

3. A process as set forth in claim 1, wherein said inner film is polyethylene.

4. A process as recited in claim 2, wherein said dissimilar materials are synthetic resins and the outer film is nylon and the inner film is nylon sclair.

5. A process as set forth in claim 4, wherein the outer film has a thickness of one millimeter and the inner film has a thickness of two millimeters.

6. A process as set forth in claim 1, wherein said outer film is nylon.

7. A process as set forth in claim 6, wherein the outer film has a thickness of one mil and the inner film has a thickness of two mils.

8. A microwave gel pack comprising:
    a completely sealed envelope constructed from opposed laminate layers portions of which are joined by sealed seams, said layers defining an inner chamber within which is disposed a gel that includes water, said chamber being sealed from the exterior of said gel pack, each of said laminate layers including a pair of co-extensive inner and outer films contacting each other throughout their surface areas, said films being of dissimilar materials; and
    said dissimilar materials being selected so that the laminate layers of said gel pack do not pass steam produced during heating of the gel within said gel pack by microwave energy at approximately full power of a microwave heating device-and do not rupture or separate at the seams thereof when subjected to said microwave energy for a period of time exceeding about two minutes but not exceeding about four minutes.

9. An article of manufacture as set forth in claim 8, wherein said dissimilar materials are synthetic resinous films, or a paper layer adhered to a resinous layer or a fabric layer adhered to a resinous layer.

10. An article of manufacture as set forth in claim 9, wherein said resinous layer is selected from the group consisting of polyethylene and polyurethane.

11. An article of manufacture as set forth in claim 8, wherein the inner and outer films are of synthetic resins and the inner film is selected from the group consisting of polyethylene and nylon sclair.

12. An article of manufacture as set forth in claim 10, wherein said outer film is nylon.

13. An article of manufacture as set forth in claim 12, wherein the outer film has a thickness of about one mil and the inner film has a thickness of about two mils.

* * * * *